(12) United States Patent
Lee

(10) Patent No.: US 9,161,495 B2
(45) Date of Patent: *Oct. 20, 2015

(54) METHOD FOR PREPARING RAW MATERIAL FOR FUNCTIONAL FOODS FROM BARLEY OR WHEAT SEEDS

(71) Applicant: Gyu-Gil Lee, Jeju-do (KR)

(72) Inventor: Gyu-Gil Lee, Jeju-do (KR)

(73) Assignee: JEJUHONGAMGA, Jeju Province (KR)

(*) Notice: Subject to any disclaimer, the term of this patent is extended or adjusted under 35 U.S.C. 154(b) by 379 days.

This patent is subject to a terminal disclaimer.

(21) Appl. No.: 13/717,571

(22) Filed: Dec. 17, 2012

(65) Prior Publication Data

US 2013/0108721 A1    May 2, 2013

Related U.S. Application Data

(63) Continuation-in-part of application No. 13/460,810, filed on Apr. 30, 2012, now Pat. No. 8,357,406, and a continuation of application No. 12/947,801, filed on Nov. 16, 2010, now abandoned.

(30) Foreign Application Priority Data

Nov. 17, 2009  (KR) .................. 10-2009-0110671

(51) Int. Cl.
*A61K 36/8998* (2006.01)
*A61K 36/00* (2006.01)
*A01G 1/00* (2006.01)
*A23L 1/30* (2006.01)
*A23L 1/105* (2006.01)
*A23L 1/172* (2006.01)
*A61K 36/899* (2006.01)

(52) U.S. Cl.
CPC ............... *A01G 1/001* (2013.01); *A23L 1/105* (2013.01); *A23L 1/1055* (2013.01); *A23L 1/172* (2013.01); *A23L 1/3002* (2013.01); *A61K 36/899* (2013.01); *A61K 36/8998* (2013.01)

(58) Field of Classification Search
None
See application file for complete search history.

(56) References Cited

U.S. PATENT DOCUMENTS

| 2,947,667 A | 8/1960 | Komm et al. |
| 2003/0039723 A1 | 2/2003 | Park |

FOREIGN PATENT DOCUMENTS

| KR | 2008-0074290 | 8/2008 |
| KR | 2010-0020123 | 2/2010 |
| KR | 2010-0059278 | 6/2010 |
| KR | 2010-0092786 | 8/2010 |
| WO | WO 91/17672 A | 11/1991 |

OTHER PUBLICATIONS

Dolgushin, Specific characteristics of winter wheat stage development under conditions of fall sowing Referat. Zhur., Biol., 1959, No. 39080. (Translation). Original Title: Osobennosti stadiinogo razvitiya ozimoi pshenitsy v usloviyakh osennego poseva Referat. Zhur., Biol., 1959, No. 39080. (Translation).*
Reda, Endogenous cytokinins in vernalized winter wheat grains. Planta (1976) vol. 130, No. 3, pp. 265-268.*
Zhao et al, Isolation of a vernalization-related cDNA clone(VRC) using mRNA differential display in winter wheat. Chinese Science Bulletin (1998), 43(14), 1201-1205.*
Rhee, et al., Lactic Acid Fermentation of Barley Malt Syrup by Lactobacillus-Acidophilus, Agricultural Chemistry and Biotechnology (1988) vol. 31, No. 3, pp. 255-260.
Chun, Variations in Rate of Leaf Emergence, Initiation of Ear Primordium, Stem Elongation and Heading Time Vernalization Duration of Barley with Differing Growth Habits. Field Crops Research (1993) vol. 32, No. 1-2. pp. 159-172.

* cited by examiner

*Primary Examiner* — Qiuwen Mi
(74) *Attorney, Agent, or Firm* — Intellectual Property Law Group LLP

(57) ABSTRACT

A method is provided for preparing a raw material for functional foods from vernalized, pre-germinated barley or wheat seeds, plumules cultured the vernalized, pre-germinated barley or wheat seeds, or a material resulting from the fermentation of the vernalized, pre-germinated barley or wheat seeds with lactic acid bacteria.

6 Claims, No Drawings

METHOD FOR PREPARING RAW MATERIAL FOR FUNCTIONAL FOODS FROM BARLEY OR WHEAT SEEDS

CROSS-REFERENCE TO RELATED APPLICATIONS

This application is a continuation-in-part of commonly owned U.S. patent application Ser. No. 13/460,810 filed on Apr. 30, 2012, which is a continuation of U.S. patent application Ser. No. 12/947,801 filed on Nov. 16, 2010, which claims benefit of priority to Korean patent application 10-2009-0110671, filed on Nov. 17, 2009. The entire contents of these prior patent applications are hereby incorporated by reference.

BACKGROUND OF THE INVENTION

1. Field of the Invention

The present invention relates to a method for preparing a raw material for functional foods from barley or wheat seeds. More particularly, the present invention relates to a method for preparing a raw material for functional foods that exhibit antioxidant, antidiabetic and/or antiobesity activity, by vernalizing barley or wheat seeds or fermenting vernalized barley or wheat seeds.

2. Description of the Related Art

Temperature is a factor which has a great influence on the photoperiodism of various crops and plants. Particularly, temperature plays an important role in flowering and developing annual winter crops or biennial crops.

Many temperature plants must experience a period of low temperature or cold of from 2 to 6 weeks to initiate or accelerate the flowering process in the spring. For example, when winter-growing species (e.g., barley, wheat, etc.) are seeded in the spring, their germination is delayed or does not occur.

Trofim Denisovich Lysenko, a soviet agronomist, advanced the theory that the length of the vegetative period of plants is dependent on not only their inheritance but also the external environment that exists when the plant is growing. He asserted that the poor germination of winter-growing crops sowed in the spring is attributed to the condition of the temperature being high after sowing, based on the finding that when they are sowed after exposure to the prolonged cold, seeds of winter-growing crops could readily germinate like spring-growing crops.

The artificial low-temperature treatment which allows winter-growing species to be sowed in the spring is termed "vernalization", and effective vernalization can be achieved at a temperature range of from 0 to 10° C.

Like photoperiodism, responses to cold exposure may be divided into qualitative and quantitative responses. Without the experience of the prolonged cold of winter, the species of qualitative responses show hibernalism, that is, the property of plants whereby they remain for an indefinitely long period in the phase of tillering without flowering stems while the species of quantitative response show delayed flowering.

Depending on treatment temperature, vernalization may be classified into low-temperature vernalization (0~10° C.) and high-temperature vernalization (10~30° C.). Also, there are two vernalization treatments according to the time of vernalization: seed vernalization and bulb vernalization which target pregerminated seeds and bulbs, respectively.

Winter-growing wheat plants such as barley, wheat, etc. are of the seed vernalization variety whereas cabbages and rapes are representative of bulb vernalization plants.

Lactic acid bacteria is the generic name for bacteria that utilize saccharides such as glucose as an energy source with the concomitant production of lactic acid. In the body, lactic acid bacteria show various beneficial functions including inhibiting the growth of harmful bacteria, bowel regulation, reducing the blood cholesterol level, anticancer activity, and ameliorating constipation and diarrhea. The genera that comprise lactic acid bacteria are at its core *Streptococcus, Pediococcus, Leuconostoc, Lactobacillus*, and *Bifidobacterium*.

Lactic acid bacteria are applied to food processing, typically aiming at improving the preservability, favor and/or functionality of foods.

For example, Korean Patent Laid-Open Publication No. 2010-0092786 discloses the antidiabetic activity of the food prepared by fermenting an extract from a mixture of Ganoderma lucidum and bitter buckwheat with *Lactobacillus*. Korean Patent Laid-Open Publication No. 2010-0059278 discloses a method for manufacturing savor-improved tea by treatment with lactic acid bacteria. The inhibitory activity of soybean fermented by complex Kimchi lactic acid bacteria against food poisoning bacteria is described in Korean Patent Laid-Open publication No. 2010-0020123. Korean Patent Laid-Open Publication No. 2008-0074290 discloses the application of lactic acid bacteria to the production of a beverage made from birch tree fluid that has improved perservability.

Leading to the present invention, intensive and thorough research into functional foods, conducted by the present inventors, resulted in the finding that when subjected to vernalization and optionally fermentation with lactic acid bacteria, barley and wheat seeds were provided with various functionalities including antioxidant activity, antidiabetic activity and antiobesity activity, higher than those of germinated seeds.

SUMMARY OF THE INVENTION

It is therefore an object of the present invention to provide a method for preparing a raw material for functional foods by vernalizing barley or wheat seeds.

It is another object of the present invention to provide a method for preparing a raw material for functional foods by vernalizing barley or wheat seeds, followed by fermentation with lactic acid bacteria.

DESCRIPTION OF THE PREFERRED EMBODIMENTS

As elucidated in the following Example Section, far higher physiological functionality (particularly, antioxidant activity, antidiabetic activity and antiobesity activity) was found in barley powder or wheat seed powder which had undergone pre-germination and vernalization, in the powder of plumules cultured from the pre-germinated, vernalized barley or wheat seeds, or in a material resulting from the fermentation of vernalized, pre-germinated barley or wheat seeds with lactic acid bacteria than was found in the powder of germinated seeds or in the powder of the plumules cultured from germinated seeds.

Particularly, fermentation with lactic acid bacteria subsequent to vernalization allows barley or wheat seeds to exhibit far higher functionalities than vernalization alone.

The reason why higher functionalities are found in vernalized barley or wheat seeds, their plumules, and lactic acid bacteria-fermented, vernalized seeds or plumules than in germinated seeds is attributed, in our opinion, to the amount of various functional materials increasing during vernalization and fermentation.

The present invention is provided on the basis of the experimental results.

In accordance with an aspect thereof, the present invention provides a method for preparing a raw material used to make a functional food, characterized by vernalizing barley or wheat seeds.

The raw material used to make a functional food according to the present invention may be prepared in either of two manners. One method comprises (a) pre-germinating barley or wheat seeds, (b) vernalizing the pre-germinated barley or wheat seeds, and (c) processing the pre-germinated, vernalized barley or wheat seeds. The other method comprises (a) pre-germinating barley or wheat seeds, (b) vernalizing the pre-germinated barley or wheat seeds, (c) cultivating the pre-germinated, vernalized barley or wheat seeds to produce barley or wheat plumules, and (d) processing the barley or wheat plumules.

As used herein, the term "functional" is intended to refer to having a positive impact on the physiological activity of the body. In this context, the functional material of the present invention was found to show the effects of reducing cholesterol level, improving hyperlipidemia, mitigating a hangover and protecting hepatic cells as well as antioxidant activity, antidiabetic activity and antiobesity activity.

As used herein, the term "pre-germination" is intended to mean sprouting seeds in advance (e.g., the corpus albicans, that is, the root primordia appears from the radicles). Proper pre-germination temperatures and periods of barley and wheat are well known in the art. Generally, pre-germination periods are shortened when pre-germination temperatures are set to be at their highs, and vice versa. For example, after seeds are allowed to absorb sufficient water, their pre-germination may be performed at 10~25° C. for 10~50 hrs or at 5~10° C. for 40~75 hrs. In an embodiment of the present invention, barley or wheat seeds are immersed in water so that they can absorb water. The seeds are then incubated at 10~25° C. for 10~24 hrs to pre-germinate 3~5% of the total number of seeds. The number of the seeds that sprout (that is, pre-germinated seeds) may range from 0.1 to 100% of the total population of the seeds. However, it is preferred if only 3~5% of the total number of seeds pre-germinate because it has a positive effect on the next vernalization step. As used herein, pre-germination contains the meanings of the concepts of sprouting or germination. As a rule, when seeds undergo vernalization, germination or sprouting is expressed as "pre-germination".

The term "vernalization", as used herein, is intended to refer to low-temperature treatment of pre-germinated barley and/or wheat seeds for a predetermined period of time. As described above, certain crops have their own sowing times. A crop which has been sowed at a time other than its own sowing time may not bloom or may bloom at a delayed time when the temperature of the external environment is not suitable for the blooming of the plant. One of the prerequisites for blooming a crop is that a suitable temperature be maintained for a predetermined period of time. Proper vernalization is dependent on temperature and time. For barley and wheat, a suitable vernalization temperature preferably falls in the range of 0~5° C., more preferably in the range of 0~3° C. Less than 0° C. guarantees only reduced vernalization effects. On the other hand, vernalization effects start to gradually decrease from 5° C. As for the vernalization period, its lower limit is 15 days, preferably 30 days and more preferably 40 days and its upper limit is 120 days, preferably 100 days, 100 days, 90 days, 80 days, 70 days, 60 day or 50 days. In an embodiment of the present invention, barley and wheat seeds were vernalized at 0~3° C. for 40~50 days. Moreover to obtain effective vernalization, humidity for vernalization preferably falls in 80~90%. Optimal vernalization temperatures and periods may be selected as a matter of course by those skilled in the art.

As used herein, the term "processing" is intended to include drying and pulverizing, or squeezing vernalized seeds or plumules, or extracting vernalized seeds or plumules with a solvent, such as distilled water, lower alcohols of 1 to 5 carbon atoms, e.g., methanol, ethanol, acetone, ethyl acetate, saturated normal butanol, chloroform, methylene chloride, water, or a mixture thereof. In the case of extracting with a solvent, the extract may be a crude extract or a fraction obtained by fractionating the crude extract with the above-mentioned solvent, or may be in a liquid or solid phase from which the solvent is removed. As long as the extraction method used includes the immersion of a target in an extraction solvent, any method may be employed. Examples of the extraction method include cold precipitation, reflux, warming, and ultrasonication.

As used herein, the term "plumule" refers to a new shoot prior to the formation of the first knar.

Unless expressly defined herein, the terminology used to describe the embodiments of the invention will be understood to have the same meaning attributed to them by those skilled in the art.

In the method for preparing a raw material for functional foods, vernalized, pre-germinated barley or wheat seeds may be directly processed and alternatively, may be cultured into plumules which are then processed. These plants may be obtained by culturing vernalized barley or wheat seeds at 10~25° C. for 15~20 days. The plumules thus obtained may be 20~30 cm in length. Such plumules may be preferably processed into powder by drying and pulverizing or into juice by squeezing.

In accordance with another aspect thereof, the present invention pertains to a method for preparing a raw material for functional foods, characterized by vernalizing pre-germinated barley or wheat seeds and fermenting the vernalized, pre-germinated barley or wheat seeds with lactic acid bacteria.

In this context, the method for preparing a raw material for functional foods comprises (a) pre-germinating barley or wheat seeds, (b) vernalizing the pre-germinated barley or wheat seeds and (c) fermenting the vernalized, pre-germinated barley or wheat seeds with lactic acid bacteria.

In this method, the step (c) of fermenting the vernalized, pre-germinated barley or wheat seeds may be carried out by saccharifying enzymes, such as α-amylase, maltase, which have been produced in the barley or wheat seeds during the pre-germination process because the enzymes degrade polysaccharides such as starch into glucose or maltose which can be used as energy sources by lactic acid bacteria.

As mentioned above, the term "lactic acid bacteria" refers to bacteria that utilize saccharides such as glucose as an energy source with the concomitant production of lactic acid and include *Streptococcus* sp., *Pediococcus* sp., *Leuconostoc* sp., *Lactobacillus* sp. and *Bifidobacterium* sp. Preferably, the lactic acid bacteria is of *Lactobacillus* sp., and more preferably of *Lactobacillus bulgaricus* and/or *Lactobacillus plantarum*.

The method of preparation of the present invention may further comprise, prior to the step (c) of fermenting the vernalized, pre-germinated barley or wheat seeds with a lactic acid bacteria, saccharifying the vernalized, pre-germinated barley or wheat seeds with a saccharifying enzyme to induce or increase the production of glucose and maltose available as an energy source by the lactic acid bacteria, the saccharifying enzyme being expressed during the pre-germination in the barley or wheat seeds and selected from among α-amylase, maltase or a combination thereof. This saccharification step is taken with the aim of reducing fermentation time or increasing fermentation efficiency.

The saccharification step can be carried out by incubating the vernalized, pre-germinated barley or wheat seeds for a predetermined period of time at such a suitable temperature as to guarantee the optimal activity of the saccharifying enzyme such as α-amylase or maltase, optionally with the addition of a saccharifying enzyme such as α-amylase or maltase. In an embodiment of the present invention, as elucidated in the following Example section, the vernalized, pre-germinated barley or wheat seeds were saccharified by incubating at 60~63° C. for 4~5 hrs without the addition of an external saccharifying enzyme, such as α-amylase or maltase. The selection of optimal temperatures and periods for saccharification and the addition of external saccharifying enzymes such as α-amylase or maltase may be determined as a matter of course by those skilled in the art.

In the saccharifying step, by-products obtained during a crop polishing process may be used in order to reinforce and supplement the functionality of the resulting fermented material. It is well known that physiologically active materials of crops are concentrated in the hulls of cereals such as rice bran, wheat bran, barley bran, etc. For better saccharification, these by-products of crop polishing may be added in an amount of from 10 to 150 parts by weight based on 100 parts by weight of the vernalized, pre-germinated barley or wheat seeds. The polysaccharides, such as starch, contained in the by-products of crops are saccharified by the saccharifying enzymes, such as α-amylase, maltase, etc. expressed in the vernalized, pre-germinated barley or wheat seeds.

The method for preparing a raw material for functional foods in accordance with the present invention may further comprises, prior to the step (c) of fermenting the vernalized, pre-germinated barley or wheat seeds with lactic acid bacteria, drying the vernalized, pre-germinated barley or wheat seeds at high temperatures to deactivate the saccharifying enzymes and/or pulverizing the vernalized, pre-germinated barley or wheat seeds so as to increase fermentation efficiency. The temperature at which the seeds are dried so as to inactivate the saccharifying enzymes and the size of particles to which the seeds are pulverized are selected as a matter of course by those skilled in the art. In an embodiment of the present invention, the seeds were dried at 80~85° C. to a water content of 8~12% and then pulverized to a particle size of 80~100 mesh.

The inactivation of saccharifying enzymes and the pulverization of the vernalized, pre-germinated barley or wheat seeds are carried out for the purpose of increasing the fermentation efficiency of lactic acid bacteria.

In addition, the method for preparing a raw material for functional foods in accordance with the present invention may further comprise, prior to the step (c) of fermenting the vernalized, pre-germinated barley or wheat seeds with lactic acid bacteria, sterilizing the vernalized, pre-germinated barley or wheat seeds to prevent bacteria other than lactic acid bacteria from inducing undesired fermentation. The sterilization may be achieved using a well-known technique, such as UV irradiation, autoclaving, etc.

In the preparation method of the present invention, the step (c) of fermenting the vernalized, pre-germinated barley or wheat seeds with lactic acid bacteria is preferably conducted sufficiently. The term "sufficiently" in association with fermentation with lactic acid bacteria, as used herein, is intended to mean pertaining to a step at which lactic acid bacteria have already proliferated maximally and thus do not grow. The period of time for which the fermenting step is conducted so as to sufficiently ferment the seeds is determined in consideration of the time and temperature of fermentation and whether the seeds have undergone the above-mentioned saccharification. The time and temperature of fermentation needed to sufficiently ferment the seeds can be determined by those of ordinary skill as part of their normal activities. In an embodiment of the present invention, the fermentation is conducted at 38~40° C. for 2 days.

In the method for preparing a raw material for functional foods in accordance with the present invention, the step (c) of fermenting the vernalized, pre-germinated barley or wheat seeds is carried out in the presence of an organic material such as skim milk, milk, grape sugar and oligosaccharides (when Bifidobacteria is used), for promoting the proliferation of the bacteria, and/or in the presence of a powder or extract of medicinal herb, such as ginseng, jujube, ginkgo, lingshi mushroom, *Coriolus versicolor, Eucommia*, angelica, chicory, comfrey, Acanthopanax, mugwort, plantain, solomon's seal, *Atractylodes japonica*, and arrowroot, and/or a powder of vegetable extract of such vegetables as tomato, Angelica utilis, and carrot for improving the functionality of the resulting fermented material.

In a preferred embodiment, the organic material such as skim milk may be added in an amount of from 2 to 10 parts by weight based on 100 parts by weight of the vernalized, pre-germinated barley or wheat seeds. The powder/extract of medicinal herb or vegetable may be added in an amount of from 1 to 5 parts by weight based on 100 parts by weight of the vernalized, pre-germinated barley or wheat seeds.

The extract is intended to include juice obtained by squeezing, and an extract obtained by extracting with methanol, distilled water, ethanol, acetone, ethylacetate, saturated normal butanol, chloroform, methylene chloride, water or a mixture thereof. Extraction with a solvent is as described above in conjugation with the term "processing".

In the method for preparing a raw material for functional foods in accordance with the present invention, the step (c) of fermenting the vernalized, pre-germinated barley or wheat seeds is conducted in the presence of yeast as well as lactic acid bacteria. The yeast useful in the present invention is *Saccharomyces* sp. Examples include *Saccharomyces rouxii, Saccharomyces cerevisiae, Saccharomyces oviformis*, and *Saccharomyces steineri*, with preference for *Saccharomyces cerevisiae*. The yeast is used to reinforce the functionality of the fermented material.

The method for preparing a raw material for functional foods in accordance with the present invention may further comprise processing the fermented material after the step (c). Aiming to process the fermented material into a phase suitable for use as a raw material for functional foods, this processing step may be carried out by filtration, drying at high temperatures, concentration in a vacuum and/or lyophilization to give a fermented material in a liquid or solid phase.

In accordance with a further aspect thereof, the present invention pertains to a functional food composition comprising at least one of (i) a processed form of the vernalized, pre-germinated barley or wheat seeds, (ii) a processed form of the plumules cultured from the vernalized, pre-germinated barley or wheat seeds, and (iii) a material resulting from the fermentation of the vernalized, pre-germinated barley or wheat seeds by lactic acid bacteria.

The fermented material may be in a processed form as a result of drying at high temperatures, concentration in a vacuum, and/or lyophilization.

The term "functional" in this context is as described above and is intended to mean pertaining to antioxidant activity, antidiabetic activity, antiobesity activity or antiobesity-derived diet functionality. Therefore, the functional food composition of the present invention should be construed as including compositions for antioxidant foods, antidiabetic foods, antiobesity foods, and diet foods.

As used herein, the term "diet" in conjunction with foods, is intended to refer to any food or drink whose recipe has been altered in some way to make it part of a body modification diet. Although the usual intention is weight loss and changing the body type, the diet composition of the present invention may be formulated to work on the beauty or health of normal persons.

The term "effective ingredient" refers to an ingredient which can exhibit a desired activity when used alone or in combination with an inactive carrier.

The functional food composition of the present invention may comprise a sweetener, a flavoring agent, a physiologically active ingredient and/or a mineral as well as the effective ingredient.

The sweetener, natural or synthetic, is used to give a sweet taste. Preferable is a natural sweetener such as a sugar sweetener. Examples of the sweetener include corn syrup, honey, sucrose, fructose, lactose, and maltose.

The flavoring agent is used to improve the taste or smell of the food and may be natural or synthetic. Preferable is a natural flavoring agent. In addition to improving the flavor of foods, a natural flavoring agent may help supplement the nutrition. Examples of the natural flavoring agent include those obtained from apple, lemon, tangerine, grape, strawberry, peach, green tea leaves, Solomon's seal, bamboo's leaves, cinnamon, chrysanthemum, jasmine, ginseng (red ginseng), bamboo shoots, aloe vera, and ginkgo. A natural flavoring agent may be a concentrate in a liquid phase or an extract in a solid phase. If necessary, a synthetic flavoring agent may be employed. Examples of the synthetic flavoring agent include esters, alcohols, aldehydes, and terpenes.

Among the physiologically active materials useful in the present invention are catechins such as catechin, epicatechin and gallocatechin, and vitamins such as retinol, ascorbic acid, tocopherol, calciferol, thiamine, and riboflavin.

Examples of the mineral useful in the present invention include calcium, magnesium, chrome, cobalt, copper, fluorides, germanium, iodine, iron, lithium, magnesium, manganese, molybdenum, phosphor, potassium, selenium, silica, sodium, sulfur, vanadium and zinc.

The food composition of the present invention, if necessary, may comprise a preservative, an emulsifier, an acidulant, and a thickener in addition to a sweetener.

As long as its effects are achieved, the additive such as a preservative, an emulsifier, etc. may be preferably added in a trace amount. Numerically, the trace amount corresponds to a range of from 0.0005 wt % to 0.5 wt % based on the total weight of the food composition.

Examples of the preservative useful in the present invention include sodium calcium sorbate, sodium sorbate, potassium sorbate, calcium benzoate, sodium benzoate, potassium benzoate, and EDTA (ethylene diamine tetraacetate).

The emulsifier useful in the present invention may be exemplified by acacia gum, carboxymethylcellulose, xanthan gum and pectin.

The acidulant useful in the present invention may be exemplified by folic acid, malic acid, fumaric acid, adipic acid, phosphoric acid, gluconic acid, tartaric acid, ascorbic acid, and acetic acid. The acidulant may be added to give suitable acidity to the food composition with the aim of inhibiting microbial growth in addition to improving the taste.

Among the thickeners that can be used are a suspending agent, a cohesive agent, a gelling agent, and a swelling agent.

The food composition of the present invention may be formulated into a powder, a juice concentrate, a beverage, a tablet, a suspension, a granule, an emulsion, a capsule and a syrup.

As described hitherto, a method is provided for preparing a raw material for functional foods from vernalized barley or wheat seeds or plumules cultured from the vernalized seeds. Also, a raw material for functional foods can be prepared from a fermented material of the vernalized, pre-germinated barley or wheat seeds using the method of the present invention.

For use in functional foods, the raw material may be formulated into a powder, a juice concentrate, a beverage, a tablet, a granule or a syrup.

The vernalized barley or wheat seeds, the plumules cultured from the seeds, and the materials resulting from fermenting the vernalized barley or wheat seeds with lactic acid bacteria are superior in physiological activity to germinated seeds. This improvement is reputed to be based on the fact that various functional materials are newly produced or increased in quantity during the vernalization or fermentation process.

A better understanding of the present invention may be obtained through the following examples which are set forth to illustrate, but are not to be construed as limiting the present invention.

Example 1

Preparation of Plumules from Vernalized Barley Seeds and Wheat Seeds 1.1 Preparation of Vernalized Barley Seeds 10 kg of selected barley seeds were immersed at 10~15° C. for 7~8 hrs in 20 L of water so that the seeds absorbed a sufficient amount of water. Then, the barley seeds were placed on a wicker tray to remove water therefrom and covered with a diver, followed by incubation at 10~25° C. for 10~24 hrs to pre-germinate 3~5% of the total number of the seeds. Thereafter, the seeds were allowed to vernalization at 0~3° C. temperature and 80~90% humidity for 40~50 days.

1-2 Preparation of Plumules of the Vernalized Barley Seeds

The vernalized barley seeds obtained in Example 1-1 were sowed in soil in a culture room and cultured at room temperature (10~25° C.) for 15~20 days to produce plumules 20~30 cm in length before the formation of the first knar.

1-3 Preparation of Vernalized Wheat Seeds 10 kg of selected wheat seeds were immersed at 10~15° C. for 9~10 hrs in 20 L of water so that the seeds absorbed a sufficient amount of water. Then, the wheat seeds were placed on a wicker tray to remove water therefrom and covered with a diver, followed by incubation at 10~25° C. for 10~24 hrs to pre-germinate 3~5% of the total number of the seeds. Thereafter, the seeds were allowed to vernalization at 0~3° C. temperature and 80~90% humidity for 40~50 days.

1-4 Preparation of Plumules of the Vernalized Wheat Seeds

The vernalized wheat seeds obtained in Example 1-3 were sowed in soil in a culture room and cultured at room temperature (10~25° C.) for 15~20 days to produce plumules 20~30 cm in length before the formation of the first knar.

Example 2

Preparation of Fermented Material from the Vernalized Barley or Wheat Seeds 2-1. Fermentation of the Vernalized Barley Seeds by Lactic Acid Bacteria The vernalized barley seeds prepared in Example 1-1 were saccharified at a temperature of 60~63° C. and a relative humidity of 80~100% for 4~5 hrs. This saccharification was performed by amylase and maltase, which had been expressed during the pre-germination of the barley seeds before the vernalization. After completion of the saccharification, the barley seeds were dried at 80~85° C. until they had a water content of 8~12%. Then, the seeds were pulverized to a particle size of 80~100 mesh. The enzymes including amylase and maltase were inactivated by the drying process.

80 parts by weight of water was mixed with 100 parts by weight of the dried and pulverized barley seeds. To this mixture was added 2 parts by weight of complex lactic acid bacteria (*L. bularicus* and *L. plantarum*), followed by fermentation at 38~40° C. for 2~3 days to give fermented barley seeds.

2-2 Fermentation of the Vernalized Wheat Seeds by Lactic Acid Bacteria

The vernalized wheat seeds prepared in Example 1-3 were saccharified at a temperature of 60~63° C. and a relative humidity of 80~100% for 4~5 hrs, as in Example 2-1. After completion of the saccharification, the wheat seeds were dried at 80~85° C. until they had a water content of 8~12%. Then, the seeds were pulverized to a particle size of 80~100 mesh. 80 parts by weight of water was mixed with 100 parts by weight of the dried and pulverized wheat seeds. To this mixture was added 2 parts by weight of complex lactic acid bacteria (*L. bularicus* and *L. plantarum*), followed by fermentation at 38~40° C. for 2~3 days to give fermented wheat seeds.

Comparative Examples

Germination of Barley and Wheat Seeds, and Preparation of Plumules from the Germinated Barley and Wheat Seeds

Comparative Example 1

Preparation of Germinated Barley Seeds 10 kg of selected barley seeds were immersed at 10~15° C. for 7~8 hrs in 20 L of water so that the seeds absorbed a sufficient amount of water. Then, the barley seeds were placed on a wicker tray to remove water therefrom and covered with a piece of cloth, followed by incubation at 10~25° C. for 10~24 hrs to germinate 3~5% of the total number of the seeds.

Comparative Example 2

Preparation of Plumules from Germinated Barley Seeds

The germinated barley seeds obtained in Comparative Example 1 were sowed in soil in a culture room and cultured at room temperature (10~25° C.) for 15~20 days to produce plumules 20~30 cm in length before the formation of the first knar.

Comparative Example 3

Preparation of Germinated Wheat Seeds 10 kg of selected wheat seeds were immersed at 10~15° C. for 9~10 hrs in 20 L of water so that the seeds absorbed a sufficient amount of water. Then, the wheat seeds were placed on a wicker tray to remove water therefrom and covered with a diver, followed by incubation at 10~25° C. for 10~24 hrs to germinate 3~5% of the total number of the seeds.

Comparative Example 4

Preparation of Plumules from Germinated Wheat Seeds

The germinated wheat seeds obtained in Comparative Example 3 were sowed in soil in a culture room and cultured at room temperature (10~25° C.) for 15~20 days to produce plumules 20~30 cm in length before the formation of the first knar.

Experimental Examples

Assays for Antioxidant, Antidiabetic and Antiobesity Activity

Experimental Example 1

Assay for Antioxidant Activity 1-1 DPPH Radical Scavenging Activity

For use in this assay, the samples prepared in the Examples and Comparative Examples were lyophilized and/or dried and pulverized into powders.

The samples were evaluated for DPPH radical scavenging activity according to the Brand-Williams method (Brand-Williams et al., Use of a free radical method to evaluate antioxidant activity. Food Sci. Technol. 28(1): 25-30, (1995)). The samples were added at various concentrations to 0.4 mM DPPH which was then incubated at room temperature for 10 min, followed by measuring absorbance at 517 nm.

DPPH radical scavenging activity was expressed as $IC_{50}$ values (concentrations at which to scavenge DPPH radicals by half), as shown in Table 1, below. The data are average±standard deviation of three measurements.

For the positive control, the commercially available antioxidant BHA (ascorbic acid, butylated hydroxy anisole) was employed.

TABLE 1

| DPPH Radical Scavenging Activity | |
|---|---|
| Sample | $IC_{50}$ (mg/ml) |
| Ex.1-1 | 1.42 ± 0.24 |
| Ex.1-2 | 1.64 ± 0.16 |
| Ex.1-3 | 2.26 ± 0.15 |
| Ex.1-4 | 2.47 ± 0.18 |
| Ex.2-1 | 0.53 ± 0.07 |
| Ex.2-2 | 0.66 ± 0.13 |
| C. Ex. 1 | 2.23 ± 0.16 |
| C. Ex. 2 | 2.85 ± 0.21 |
| C. Ex. 3 | 3.25 ± 0.24 |
| C. Ex. 4 | 3.74 ± 0.17 |
| BHA | 0.62 ± 0.11 |

As seen in Table 1, the germinated barley or wheat seeds/plumules of the Comparative Examples, the vernalized barley or wheat seeds/plumules of Example 1, and the vernalized barley or wheat seeds fermented by lactic acid bacteria of Example 2 are arranged in increasing order of DPPH radical scavenging activity. Particularly, the fermented, vernalized barley and wheat seeds were found to show higher antioxidant activity than BHA.

1-2 Superoxide Anion Radical Scavenging Activity

Superoxide anion radical scavenging activity was evaluated by the NBT (nitro blue tetrazolium) reduction method in which NBT is reduced by the superoxide anion radicals formed in a xanthine/xanthine oxydase system.

Along with 25 mU/mL of xanthine oxidase, the samples were added at various concentrations to 1.5 mL of a reaction solution containing 50 mM potassium phosphate buffer (pH 7.8), 0.05 mM xanthine, and 0.6 mM NBT, and incubated at 25° C. for 20 min before measuring absorbance at 560 nm.

Superoxide anion radical scavenging activity was expressed as $IC_{50}$ values (concentrations at which to scavenge superoxide anion radicals by half), as shown in Table 2, below. The data are average±standard deviation of three measurements.

For a positive control, the commercially available antioxidant BHA (ascorbic acid, butylated hydroxy anisole) was employed.

TABLE 2

Superoxide Anion Radical Scavenging Activity

| Sample | $IC_{50}$ (mg/ml) |
|---|---|
| Ex.1-1 | 2.26 ± 0.25 |
| Ex.1-2 | 2.42 ± 0.17 |
| Ex.1-3 | 2.75 ± 0.14 |
| Ex.1-4 | 2.87 ± 0.23 |
| Ex.2-1 | 0.64 ± 0.18 |
| Ex.2-2 | 0.67 ± 0.21 |
| C. Ex. 1 | 3.27 ± 0.12 |
| C. Ex. 2 | 3.64 ± 0.19 |
| C. Ex. 3 | 3.93 ± 0.21 |
| C. Ex. 4 | 4.16 ± 0.13 |
| BHA | 1.12 ± 0.24 |

There is a similar pattern between the data of Table 2 and Table 1. In Table 2, the germinated barley or wheat seeds/plumules of the Comparative Examples, the vernalized barley or wheat seeds/plumules of Example 1, and the vernalized barley or wheat seeds fermented by lactic acid bacteria of Example 2 are arranged in increasing order of superoxide anion radical scavenging activity. Particularly, the fermented, vernalized barley and wheat seeds were found to show higher superoxide anion radical scavenging activity than BHA.

1-3 Inhibitory Activity Against Xanthine Oxidase

Inhibitory activity against xanthine oxidase was evaluated by the level of the uric acid produced in the xanthine/xanthine oxidase system, which can be quantitatively analyzed by absorbance at 290 nm.

100 μL of 200 mM phosphate buffer (pH 7.5) containing 0.5 mM xanthine and 1 mM EDTA was mixed with 100 μL of the samples (1 mg/mL) to which 50 mU/ml xanthine oxidase was then added to induce the production of uric acid. The produced uric acid was quantitatively analyzed by absorbance at 290 nm.

The data show in Table 3 is average±standard deviation of three measurements.

Allopurinol, a xanthine isomerase inhibitor used to treat gout, was used as a positive control.

TABLE 3

Anti-Xanthine Oxidase Activity

| Sample | Xanthine oxidase Inhibition (%) |
|---|---|
| Ex.1-1 | 11.5 ± 3.1 |
| Ex.1-2 | 10.7 ± 2.9 |
| Ex.1-3 | 7.7 ± 2.5 |
| Ex.1-4 | 6.2 ± 2.1 |
| Ex.2-1 | 28.4 ± 2.7 |
| Ex.2-2 | 19.7 ± 3.2 |
| C. Ex. 1 | 3.1 ± 2.5 |
| C. Ex. 2 | 2.1 ± 1.8 |
| C. Ex. 3 | 2.4 ± 2.2 |
| C. Ex. 4 | 2.6 ± 1.7 |
| Allopurinol | 88.2 ± 2.1 |

It is apparent that the data of Table 3 is also consistent with those of Tables 1 and 2. The vernalized barley or wheat seeds fermented by lactic acid bacteria of Example 2, although lower in inhibitory activity against xanthine oxidase than the positive control allopurinol, have greater inhibitory activity than do the germinated barley or wheat seeds/plumules of the Comparative Examples and the vernalized barley or wheat seeds/plumules of Example 1.

Experimental Example 2

Antidiabetic Activity

Streptozotocin (N-[methylnitrosocarbamoyl]-D-glucosamine, hereinafter referred to as "STZ") was intraperitoneally injected twice at a dose of 50 mg/kg at regular intervals of 2 hrs into ICR mice weighing around 250 g to induce hyperglycemia. Hyperglycemia-induced mice were used as test animals.

The samples (lyophilized and/or dried and pulverized powders) were dissolved in 1% Tween 80 (v/v in water) and administered at a dose of 100 mg/kg once a day for 30 days. During the experiment, the test animals were bred at a temperature of 18±2° C. and a relative humidity of 60±5% on light-dark (12L/12D) cycles and given free access to food and water.

After 30 days, blood was taken from the tail vein of the test animals and measured for sugar level using a glucometer (Bayer Co., USA).

The results are summarized in Table 4, below.

TABLE 4

Change in Blood Sugar Level (mg/dL)

| Sample | After 30 days |
|---|---|
| Normal | 73.3 ± 6.72 |
| Control (Diabetes induced) | 264.5 ± 11.64 |
| Diabetes induced + Ex. 1-1 Sample administered | 145.3 ± 9.41** |
| Diabetes induced + Ex. 1-2 Sample administered | 166.8 ± 13.53** |
| Diabetes induced + Ex. 1-3 Sample administered | 154.9 ± 10.17** |
| Diabetes induced + Ex. 1-4 Sample administered | 172.8 ± 8.65** |
| Diabetes induced + Ex. 2-1 Sample administered | 117.6 ± 7.32** |
| Diabetes induced + Ex. 2-2 Sample administered | 128.5 ± 9.21** |
| Diabetes induced + C. Ex. 1 Sample administered | 224.7 ± 12.16** |
| Diabetes induced + | 232.8 ± 11.38* |

TABLE 4-continued

Change in Blood Sugar Level (mg/dL)

| Sample | After 30 days |
|---|---|
| C. Ex. 2 Sample administered Diabetes induced + C. Ex. 3 Sample administered | 245.2 ± 14.92 |
| Diabetes induced + C. Ex. 4 Sample administered | 238.5 ± 9.48* |

Significance tests were done at 5% and 1% levels with paired T-test.
*$p < 0.5$,
**$p < 0.01$ Consistent with the results of the above experiments, the data of Table 4 demonstrate that both vernalization alone, and fermentation with lactic acid bacteria after vernalization bring about a reduction in blood sugar level.

Experimental Example 3

Antiobesity Activity

Male, Sprague-Dawley rats, weighing around 210, in 6 weeks after birth, were fed with a high-fat diet alone for a control and in combination with the barley and wheat seeds/plumules of the Examples and the Comparative Examples for experimental groups.

A general foodstuff (AIN-93G, Feedlab) mixed at a weight ratio of 100:10 with whole milk powder was used as the high-fat diet for the control while a mixture of 100:10:10 (w/w/w) the general foodstuff:whole milk powder:the powder of the Examples or the Comparative Examples (lyophilized or dried and pulverized powder) was used for the experimental groups.

During the experiment, the breeding room was maintained at a temperature of 18±2° C. and a relative humidity of 60±5%, under day-dark (12L/12D) cycles, with free access to food and water.

After carrying out breeding for 6 weeks, the rats in each group were measured for changes in body weight (MEAN±SD) and the results are summarized in Table 5, below.

TABLE 5

Change in Body Weight (unit:g)

| Sample | Weight Gain |
|---|---|
| Control (high-fact diet) | 212.9 ± 14.73 |
| Ex. 1-1 Sample administered | 110.4 ± 16.72** |
| Ex. 1-2 Sample administered | 126.5 ± 12.16** |
| Ex. 1-3 Sample administered | 117.9 ± 19.41** |
| Ex. 1-4 Sample administered | 131.4 ± 14.27** |
| Ex. 2-1 Sample administered | 95.7 ± 12.14** |
| Ex. 2-2 Sample administered | 104.6 ± 14.5** |
| C. Ex. 1 Sample administered | 189.4 ± 12.48** |
| C. Ex. 2 Sample administered | 193.5 ± 15.82** |
| C. Ex. 3 Sample administered | 172.1 ± 18.67** |
| C. Ex. 4 Sample administered | 169.2 ± 11.36** |

Significance tests were done at 5% and 1% levels with paired T-test.
*$p < 0.5$,
**$p < 0.01$ The data of Table 5, similar to that of Table 4, show that vernalization alone, or fermentation with lactic acid bacteria subsequent to vernalization imparted the seeds or plumules with antiobesity activity.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for increasing a functionality of barley or wheat seeds, comprising:
    (a) pre-germinating barley or wheat seeds; and
    (b) increasing the functionality of the pre-germinating barley or wheat seeds by vernalizing the pre-germinated barley or wheat seeds;
    wherein the functionality is a functionality selected from the group consisting of antioxidant activity, an antiobesitic activity and an anti-diabetic activity wherein the pre-germinating step is carried out by immersing barley or wheat seeds in water so that the seeds absorb a sufficient amount of water, and incubating the barley or wheat seeds at 10-25° C. for 10-24 hours to sprout 3-5% of a total number of the seeds.

2. The method according to claim 1, wherein the vernalizing step is carried out by incubating the pre-germinated barley or wheat seeds at 0~3° C. temperature and 80~90% humidity for 40~50 days.

3. The method according to claim 1, further comprising processing the pre-germinated, vernalized barley or wheat seeds, wherein the processing step is carried out by drying and pulverizing, or squeezing the vernalized barley or wheat seeds, or extracting the vernalized barley or wheat seeds with a solvent selected from among lower alcohols of 1 to 5 carbon atoms, acetone, ethyl acetate, saturated normal butanol, chloroform, methylene chloride, water, and a mixture thereof.

4. The method according to claim 1, further comprising cultivating the pre-germinated, vernalized barley or wheat seeds to produce barley or wheat plumules.

5. The method according to claim 4, further comprising processing the barley or wheat plumules, wherein the processing step is carried out by drying and pulverizing, or squeezing the vernalized barley or wheat plumules, or extracting the vernalized barley or wheat plumules with a solvent selected from among lower alcohols of 1 to 5 carbon atoms, acetone, ethyl acetate, saturated normal butanol, chloroform, methylene chloride, water, and a mixture thereof.

6. The method according to claim 4, wherein the plumules are new shoots before a first knar is formed, and the cultivating step is carried out by incubating the vernalized barley or wheat seeds at 10~25° C. for 15~20 days.

* * * * *